United States Patent
Krulevitch et al.

(10) Patent No.: US 7,810,233 B2
(45) Date of Patent: Oct. 12, 2010

(54) SYSTEM OF FABRICATING A FLEXIBLE ELECTRODE ARRAY

(75) Inventors: Peter Krulevitch, Pleasanton, CA (US);
Dennis L. Polla, Roseville, MN (US);
Mariam N. Maghribi, Davis, CA (US);
Julie Hamilton, Tracy, CA (US); Mark S. Humayun, La Canada, CA (US);
James D. Weiland, Valencia, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 843 days.

(21) Appl. No.: 11/545,190

(22) Filed: Oct. 10, 2006

(65) Prior Publication Data

US 2007/0142878 A1    Jun. 21, 2007

Related U.S. Application Data

(60) Division of application No. 10/115,676, filed on Apr. 3, 2002, now abandoned, which is a continuation of application No. 09/992,248, filed on Nov. 16, 2001, now Pat. No. 7,146,221.

(51) Int. Cl.
*H05K 3/30* (2006.01)

(52) U.S. Cl. ............................. 29/832; 29/831; 29/837; 29/842; 29/852; 29/885; 257/133; 257/527; 607/36; 607/37; 607/53; 607/54; 607/116; 623/24; 623/25; 623/53; 623/900; 623/901

(58) Field of Classification Search ............... 29/592.1, 29/831, 832, 837, 842, 852, 854, 885; 257/133, 257/527; 607/36, 37, 53, 54, 116, 141, 142; 623/24, 25, 53, 900, 901, 905–907, 926
See application file for complete search history.

(56) References Cited

U.S. PATENT DOCUMENTS

| 4,573,481 | A | 3/1986 | Bullara ........................ 128/784 |
| 4,969,468 | A | 11/1990 | Byers et al. |
| 5,024,223 | A | 6/1991 | Chow .......................... 128/419 |
| 5,397,350 | A | 3/1995 | Chow et al. .................... 623/4 |
| 5,749,912 | A | 5/1998 | Zhang et al. ................... 607/57 |
| 5,957,958 | A | 9/1999 | Schulman et al. ............. 607/56 |
| 6,052,624 | A | 4/2000 | Mann .......................... 607/46 |
| 6,119,044 | A | 9/2000 | Kuzma ........................ 607/137 |
| 6,129,753 | A | 10/2000 | Kuzma ........................ 607/137 |
| 6,144,883 | A | 11/2000 | Kuzma ........................ 607/137 |
| 6,230,057 | B1 | 5/2001 | Chow et al. .................... 607/54 |
| 6,298,270 | B1 | 10/2001 | Nisch et al. |
| 6,324,429 | B1 | 11/2001 | Shire et al. |
| 6,596,569 | B1 | 7/2003 | Bao et al. |
| 6,663,820 | B2 * | 12/2003 | Arias et al. .................. 264/496 |
| 6,692,680 | B2 * | 2/2004 | Lee et al. ..................... 264/485 |

* cited by examiner

*Primary Examiner*—Paul D Kim
(74) *Attorney, Agent, or Firm*—Eddie E. Scott; John H. Lee

(57) ABSTRACT

An image is captured or otherwise converted into a signal in an artificial vision system. The signal is transmitted to the retina utilizing an implant. The implant consists of a polymer substrate made of a compliant material such as poly(dimethylsiloxane) or PDMS. The polymer substrate is conformable to the shape of the retina. Electrodes and conductive leads are embedded in the polymer substrate. The conductive leads and the electrodes transmit the signal representing the image to the cells in the retina. The signal representing the image stimulates cells in the retina.

14 Claims, 9 Drawing Sheets

SYSTEM OF FABRICATING A FLEXIBLE ELECTRODE ARRAY

CROSS-REFERENCE TO RELATED APPLICATIONS

This application is a divisional of U.S. patent application Ser. No. 10/115,676, filed Apr. 3, 2002 now abandoned titled "Flexible Electrode Array for Artificial Vision," which was a continuation of U.S. patent application Ser. No. 09/992,248 filed Nov. 16, 2001, now U.S. Pat. No. 7,146,221 titled "Flexible Electrode Array for Artificial Vision."

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to electrodes and more particularly to an electrode array that can be used for artificial vision, that can be implanted, that is useful for surgical insertion, that can be attached to the surface of the skin, that can be used as a flex circuit, and that can be used in other ways.

2. State of Technology

U.S. Pat. No. 4,573,481 for an implantable electrode array by Leo A. Bullara, patented Mar. 4, 1986 provides the following background information, "It has been known for almost 200 years that muscle contraction can be controlled by applying an electrical stimulus to the associated nerves. Practical long-term application of this knowledge, however, was not possible until the relatively recent development of totally implantable miniature electronic circuits which avoid the risk of infection at the sites of percutaneous connecting wires. A well-known example of this modern technology is the artificial cardiac pacemaker which has been successfully implanted in many patients. Modern circuitry enables wireless control of implanted devices by wireless telemetry communication between external and internal circuits. That is, external controls can be used to command implanted nerve stimulators to regain muscle control in injured limbs, to control bladder and sphincter function, to alleviate pain and hypertension, and to restore proper function to many other portions of an impaired or injured nerve-muscle system. To provide an electrical connection to the peripheral nerve which controls the muscles of interest, an electrode (and sometimes an array of multiple electrodes) is secured to and around the nerve bundle. A wire or cable from the electrode is in turn connected to the implanted package of circuitry."

U.S. Pat. No. 6,052,624 for a directional programming for implantable electrode arrays by Carla M. Mann, patented Apr. 18, 2000 provides the following background information, "Within the past several years, rapid advances have been made in medical devices and apparatus for controlling chronic intractable pain. One such apparatus involves the implantation of an electrode array within the body to electrically stimulate the area of the spinal cord that conducts electrochemical signals to and from the pain site. The stimulation creates the sensation known as paresthesia, which can be characterized as an alternative sensation that replaces the pain signals sensed by the patient. One theory of the mechanism of action of electrical stimulation of the spinal cord for pain relief is the "gate control theory". This theory suggests that by simulating cells wherein the cell activity counters the conduction of the pain signal along the path to the brain, the pain signal can be blocked from passage. Spinal cord stimulator and other implantable tissue stimulator systems come in two general types: "RF" controlled and fully implanted. The type commonly referred to as an "RF" system includes an external transmitter inductively coupled via an electromagnetic link to an implanted receiver that is connected to a lead with one or more electrodes for stimulating the tissue. The power source, e.g., a battery, for powering the implanted receiver-stimulator as well as the control circuitry to command the implant is maintained in the external unit, a hand-held sized device that is typically worn on the patient's belt or carried in a pocket. The data/power signals are transcutaneously coupled from a cable-connected transmission coil placed over the implanted receiver-stimulator device. The implanted receiver-stimulator device receives the signal and generates the stimulation. The external device usually has some patient control over selected stimulating parameters, and can be programmed from a physician programming system."

U.S. Pat. No. 6,230,057 for a multi-phasic microphotodiode retinal implant and adaptive imaging retinal stimulation system by Vincent Chow and Alan Chow, patented May 8, 2001 and assigned to Optobionics Corporation provides the following background information, "A variety of retinal diseases cause vision loss or blindness by destruction of the vascular layers of the eye including the choroid, choriocapillaris, and the outer retinal layers including Bruch's membrane and retinal pigment epithelium. Loss of these layers is followed by degeneration of the outer portion of the inner retina beginning with the photoreceptor layer. Variable sparing of the remaining inner retina composed of the outer nuclear, outer plexiform, inner nuclear, inner plexiform, ganglion cell and nerve fiber layers, may occur. The sparing of the inner retina allows electrical stimulation of this structure to produce sensations of light. Prior efforts to produce vision by electrically stimulating various portions of the retina have been reported. One such attempt involved an externally powered photosensitive device with its photoactive surface and electrode surfaces on opposite sides. The device theoretically would stimulate the nerve fiber layer via direct placement upon this layer from the vitreous body side. The success of this device is unlikely due to it having to duplicate the complex frequency modulated neural signals of the nerve fiber layer. Furthermore, the nerve fiber layer runs in a general radial course with many layers of overlapping fibers from different portions of the retina. Selection of appropriate nerve fibers to stimulate to produce formed vision would be extremely difficult, if not impossible. Another device involved a unit consisting of a supporting base onto which a photosensitive material such as selenium was coated. This device was designed to be inserted through an external scleral incision made at the posterior pole and would rest between the sclera and choroid, or between the choroid and retina. Light would cause a potential to develop on the photosensitive surface producing ions that would then theoretically migrate into the retina causing stimulation. However, because that device had no discrete surface structure to restrict the directional flow of charges, lateral migration and diffusion of charges would occur thereby preventing any acceptable resolution capability. Placement of that device between the sclera and choroid would also result in blockage of discrete ion migration to the photoreceptor and inner retinal layers. That was due to the presence of the choroid, choriocapillaris, Bruch's membrane and the retinal pigment epithelial layer all of which would block passage of those ions. Placement of the device between the choroid and the retina would still interpose Bruch's membrane and the retinal pigment epithelial layer in the pathway of discrete ion migration. As that device would be inserted into or through the highly vascular choroid of the posterior pole, subchoroidal; intraretinal and intraorbital hemorrhage would likely result along with disruption of blood flow to the posterior pole. One such device was reportedly constructed and implanted into a patient's eye resulting in light perception but not formed imagery. A photovoltaic device artificial retina was also disclosed in U.S. Pat. No. 5,024,223. That device was inserted into the potential space within the retina itself. That space, called the subretinal space, is located between the outer and inner layers of the retina. The device was comprised of a plurality of so-called Surface Electrode Microphotodiodes ("SEMCPs") deposited on a single silicon crystal substrate. SEMCPs transduced light into small electric currents that stimulated overlying and surrounding inner retinal cells. Due to the solid substrate nature of the SEMCPs, blockage of nutrients from the choroid to the inner retina occurred. Even with fenestrations of various geometries, permeation of oxygen and biological substances was not optimal. Another method for a photovoltaic artificial retina device was reported in U.S. Pat. No. 5,397,350, which is incorporated herein by reference. That device was comprised of a plurality of so-called Independent Surface Electrode Microphotodiodes (ISEMCPs), disposed within a liquid vehicle, also for placement into the subretinal space of the eye. Because of the open spaces between adjacent ISEMCPs, nutrients and oxygen flowed from the outer retina into the inner retinal layers nourishing those layers. In another embodiment of that device, each ISEMCP included an electrical capacitor layer and was called an ISEMCP-C. ISEMCP-Cs produced a limited opposite direction electrical current in darkness compared to in the light, to induce visual sensations more effectively, and to prevent electrolysis damage to the retina due to prolonged monophasic electrical current stimulation. These previous devices (SEMCPs, ISEMCPs, and ISEMCP-Cs) depended upon light in the visual environment to power them. The ability of these devices to function in continuous low light environments was, therefore, limited. Alignment of ISEMCPs and ISEMCP-Cs in the subretinal space so that they would all face incident light was also difficult."

SUMMARY OF THE INVENTION

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an electrode array system. The system uses a substrate with embedded electrodes and conductive leads for directly stimulating cells. The electrode array system can conform to various shapes. The electrode array has many uses. For example the electrode array system of the present invention provides an artificial vision system. The electrode array system of the present invention can provide an electrode array that is implantable and can be used for surgical insertion. Also, the electrode array system of the present invention can provide an electrode array that can be attached to the surface of the skin. The electrode array system of the present invention can provide an electrode array that can be used in other ways. Other applications of the electrode array system of the present invention include use of the electrode array as a flex circuit.

In one embodiment, a method is provided for processing an electrode array. The method includes implementing initial processing steps on a substrate, depositing and/or plating a conductive material on the substrate, and implementing final processing steps on the substrate. In one embodiment the substrate material is compliant. In another embodiment the substrate material is flexible. In another embodiment the substrate material is stretchable. In another embodiment the substrate material is flexible and stretchable. In another embodiment the substrate material and the conductive material is biocompatable. In another embodiment the substrate material and the conductive material is implantable. In another embodiment the conductive material is gold. In another embodiment the conductive material is platinum. In another embodiment the conductive material is gold with an underlying adhesion layer of titanium.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
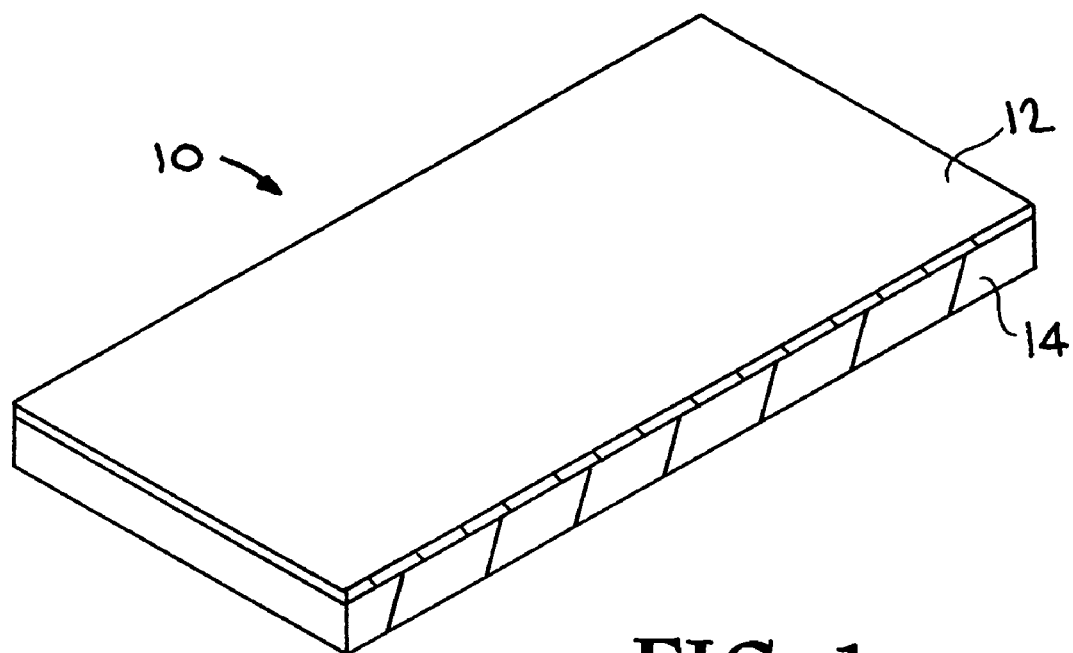
FIG. 1 illustrates a step of an electrode array fabrication process wherein an electroplating seed layer is deposited onto a handle wafer.
Figure 2:
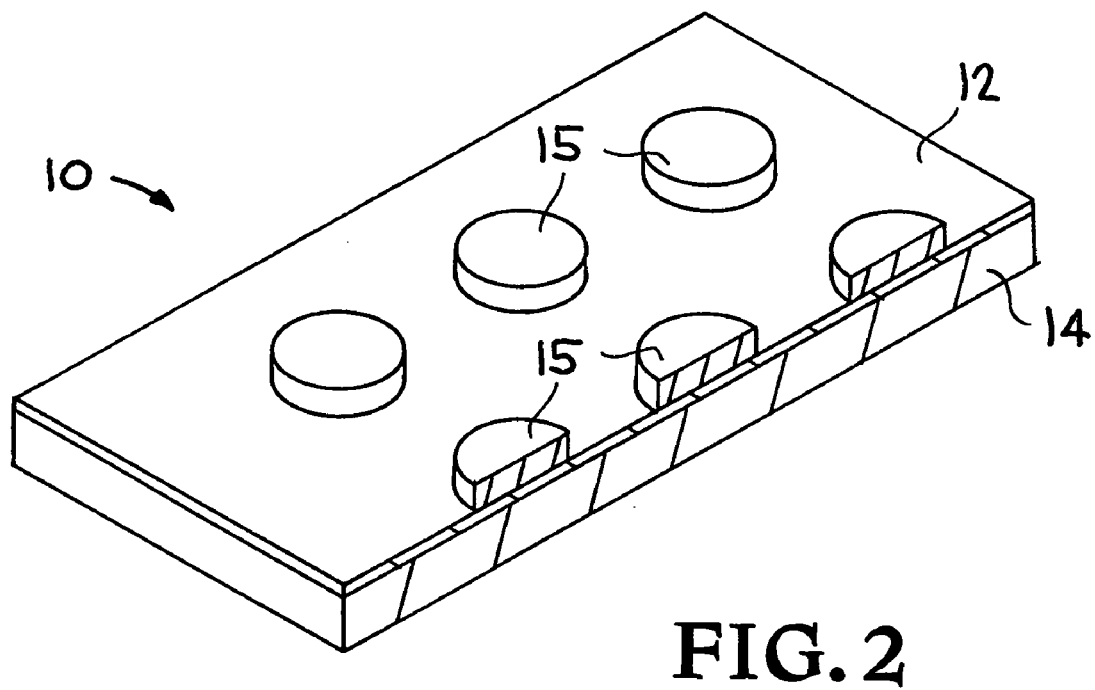
FIG. 2 illustrates a step of an electrode array fabrication process wherein a patterned photoresist is produced.

Referring now to the drawings, to the following detailed information, and to incorporated materials; a detailed description of the invention, including specific embodiments, is presented. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides an electrode array for artificial vision and a system that can be attached to the skin, can be implanted, and has many other uses. In one embodiment an electrode array is provided utilizing a substrate made of a compliant material. Electrodes and conductive leads are embedded in the substrate. The fact that the device can conform to various shapes is advantageous. In one embodiment an electrode array is provided utilizing a substrate made of a stretchable material. The fact that the electrode array is stretchable is advantageous because it will resist damage during handling. The substrate contains embedded electrodes of a conductive material.

The electrode array has many uses. For example the electrode array system provides an electrode array system with embedded electrodes and conductive leads for directly stimulating cells. The electrode array system can provide a system that is implantable and can be used for surgical insertion. The electrode array system can also be attached to the surface of the skin or other tissue. The electrode array system can be used in other ways. Other applications of the electrode array system include use as a flex circuit. The electrode array has uses including shaped acoustic sensors and transmitters and formed biological sensors and stimulators for interfacing with the human body. These can be used for applications ranging from non-destructive evaluation to sensors for virtual reality simulators. An implantable electrode array is shown in U.S. Pat. No. 4,573,481 by Leo A. Bullara, patented Mar. 4, 1986. The disclosure of this patent is incorporated herein in its entirety by reference. A directional programming for implantable electrode arrays is shown in U.S. Pat. No. 6,052,624 for by Carla M. Mann, patented Apr. 18, 2000. The disclosure of this patent is incorporated herein in its entirety by reference. A multi-phasic microphotodiode retinal implant and adaptive imaging retinal stimulation system, patented May 8, 2001, is shown in U.S. Pat. No. 6,230,057 by Vincent Chow and Alan Chow. The disclosure of this patent is incorporated herein in its entirety by reference. A photovoltaic artificial retina device is in U.S. Pat. No. 5,397,350. The disclosure of this patent is incorporated herein in its entirety by reference.

Descriptions of Specific Embodiments

Referring now to FIGS. 1 through 8, embodiments of the present invention's methods of producing electrode array systems and electrode array systems constructed in accordance with the present invention are shown. Electrode systems constructed in accordance with the embodiments shown in FIGS. 1 through 8 were constructed and successfully tested. As shown in FIGS. 1-8, embodiments of the present invention provide a processing method and an electrode array for connection to tissue. The electrode array includes a substrate composed of a polymer. The polymer has the ability to conform to various shapes of the tissue. In one embodiment the polymer is compliant. In another embodiment the polymer is an elastomer. In another embodiment the polymer is an elastomer that is flexible and stretchable. In another embodiment the elastomer is liquid silicone rubber (LSR). In another embodiment the elastomer is poly(dimethylsiloxane) or PDMS.

Electrodes are embedded in the substrate for contacting the tissue. Conductive leads are connected to the electrodes. The electrodes are useful for stimulating the cells. In one embodiment the conductive leads are connected to a device for transferring a visual image signal. In one embodiment the cells are retina cells. In one embodiment the substrate is composed of an elastomer and has the ability to conform to the shape of the retina tissue.

One embodiment of the present invention provides a system of fabricating a conformable electrode array. The system comprises the steps of spin-coating a PDMS layer onto a handle wafer that has been pre-coated with a conductive seed layer. The PDMS is patterned to expose the conductive seed layer to form electrodes. One embodiment includes the step of directly embedding an electrical connector into the device to interface with electronics. Another embodiment includes the step of casting a PDMS capping layer on to the first PDMS. Another embodiment includes the step of spinning on a PDMS capping layer to said PDMS. Another embodiment includes the step of bonding a PDMS capping layer to the first PDMS. In one embodiment the conductive seed layer is biocompatible. In another embodiment the conductive seed layer is gold. In another embodiment the conductive seed layer is platinum. In another embodiment the conductive seed layer is a conductive polymer material. In another embodiment a pre-patterned or formed PDMS layer is bonded to the handle wafer. In another embodiment a pre-patterned or formed PDMS layer is cast in place with a mold. In another embodiment the conductive seed layer is electroplated using gold. In another embodiment the conductive seed layer is electroplated using platinum. In another embodiment a step of patterning conducting lines on the PDMS is performed using thin film deposition. The conducting lines are patterned using a combination of thin film deposition and photolithography. In another embodiment the step of patterning conducting lines on the PDMS is conducted using photolithography. In another embodiment the step of patterning conducing lines on the PDMS is conducted using shadow masking. An embodiment includes doping the PDMS with metal particles to selectively render it conductive. An embodiment includes removing the PDMS from the handle wafer.

The flexible electrode array 10 shown in FIGS. 1-8 is produced by implementing various processing steps on a substrate. A conductive material 12 is deposited on the handle wafer 14 and various processing steps are taken to complete the flexible electrode array 10. The thin film conductive layer can be deposited by evaporation. The flexible electrode array system, generally designated by the reference numeral 10, includes a poly(dimethylsiloxane) or PDMS (a form of silicone rubber) substrate 11 with embedded electrodes and conductive leads. The substrate 11 is initially positioned on a handle wafer 14.

The steps illustrated in FIGS. 1-8 and described below were used for constructing the flexible electrode array 10. The electrode system was constructed using a combination of electroplating, and deposition, and patterning of thin film metals on PDMS.

Electrode Fabrication Process

1. Deposit Gold 12 (or Platinum) on to handle wafer 14 as shown in FIG. 1. This provides an electroplating seed layer and allows for removal of the PDMS from the substrate after processing.

2. Spin on thick photoresist 15.

3. Expose through mask and develop to produce the patterned photoresist shown in FIG. 2.

4. Mix PDMS 10:1 ratio resin to curing agent. Mix well and degas.

Figure 3:
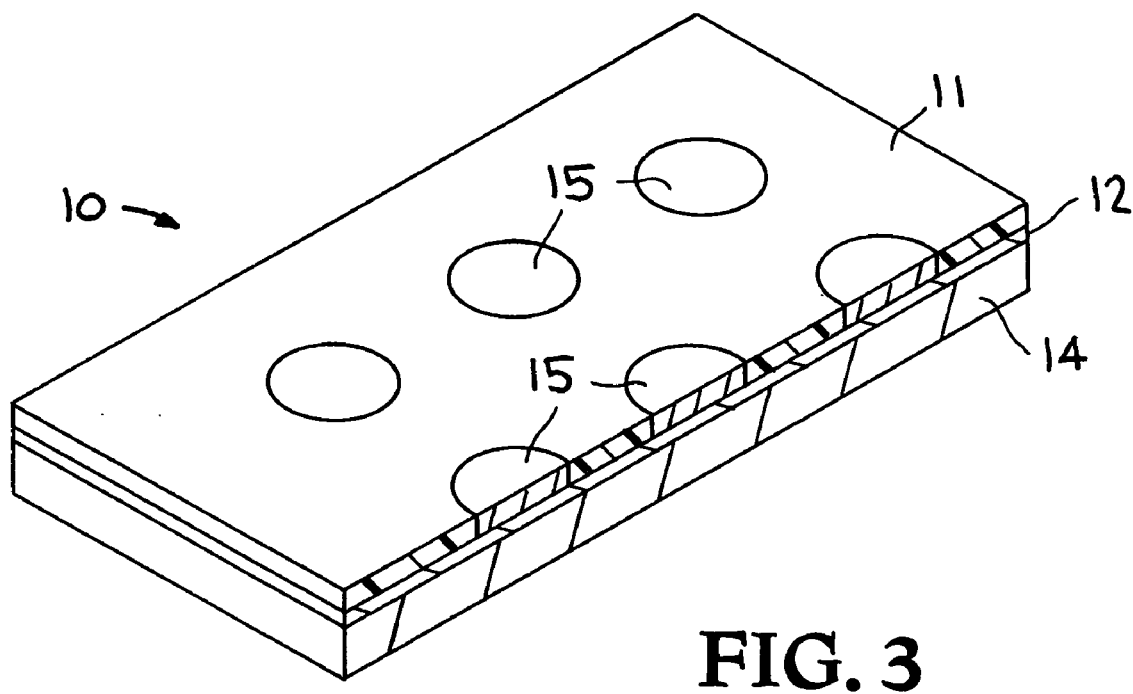
FIG. 3 illustrates a step of an electrode array fabrication process wherein a polymer is such as poly(dimethylsiloxane)—PDMS (a form of silicone rubber)—is spun or cast onto the patterned photoresist on the handle wafer.

5. Spin on or cast desired thickness of PDMS 11 onto the patterned photoresist on the handle wafer, preferably round wafers 15 to make later processing steps easier, as shown in FIG. 3.

6. Let PDMS settle at room temperature before curing. This allows PDMS to separate from the photoresist.

7. Cure PDMS 1 hr at 66° C.

8. Allow PDMS to cool.

Figure 4:
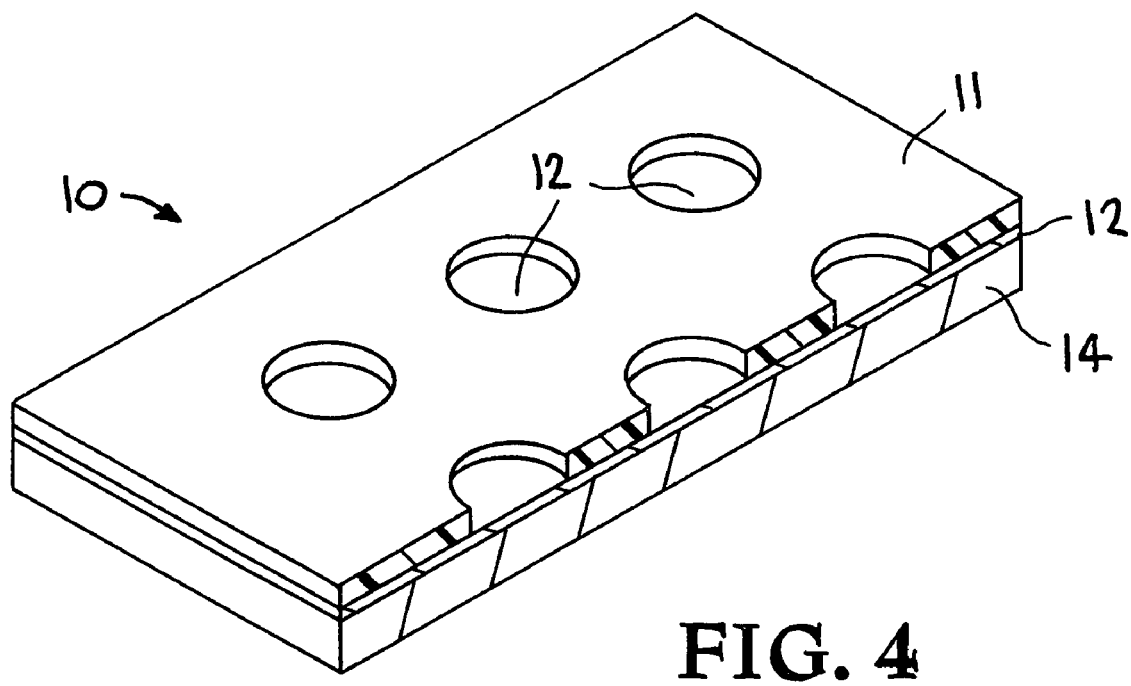
FIG. 4 illustrates a step of an electrode array fabrication process wherein the remaining photoresist is removed resulting in patterned PDMS on top of the handle wafer, revealing sections of the underlying seed layer.

9. Remove remaining photoresist using acetone. This results in patterned PDMS 11 on top of handle wafer with a partially exposed seed layer 12 as shown in FIG. 4.

Figure 5:
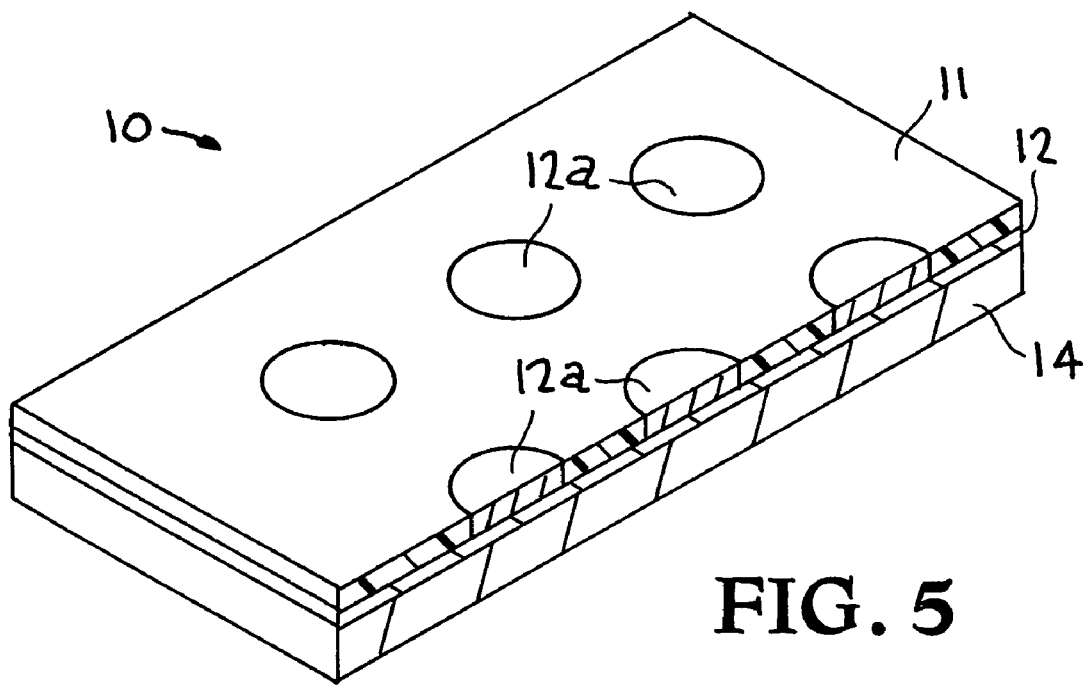
FIG. 5 illustrates a step of an electrode array fabrication process wherein gold or platinum is electroplated through the patterned PDMS to form electrodes.

10. Electroplate gold or platinum through the patterned PDMS to form electrodes 12a as shown in FIG. 5 by plating said electrodes slightly higher than the thickness of said PDMS until said electrodes form slight mushroom caps which later will prevent said electrodes from popping out of said PDMS when said PDMS is removed from said handle wafer.

Figure 6:
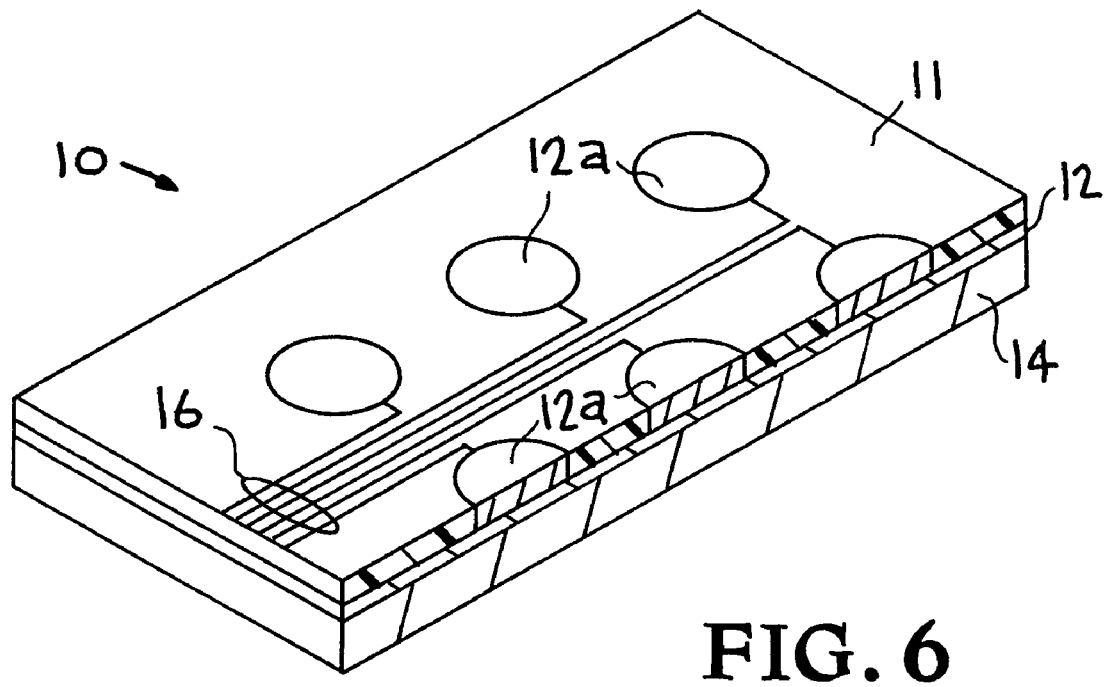
FIG. 6 illustrates a step of an electrode array fabrication process wherein conductive metal lines are patterned on the PDMS.

11. The next step is to pattern the conductive metal lines 16 on the PDMS 11 as shown in FIG. 6.

Process for Patterning Conductive Metal Lines Using Lift-Off Process

1. Oxidize the PDMS surface for 1 min. at 100 watts RF power.

2. Spin on AZ1518 Photoresist at 1000 rpm for 20 sec.

3. Soft bake the resist at 60° C. for 10 min then bring down temperature to 45° C. for 10 min and then bring down temperature to 30° C. for 10 min. (Lowering the temperature slowly minimizes cracking in the photoresist).

4. Expose for 15 sec. through mask.

5. Develop in AZ developer for approximately 1 min.

6. Deposit metal using electron-beam evaporator.

7. Deposit 200 angstroms of titanium as the adhesion layer at 2 angstroms/sec.

8. Deposit 1000 angstroms of gold as the conductive metal at 2 angstroms/sec. (another metal that can be used is platinum).

9. Deposit 200 angstroms of titanium on top of the gold to provide an adhesion layer for the $2^{nd}$ PDMS layer that will be deposited later.

10. Following metal deposition place in acetone to remove excess metal through lift-off process, but do not shake or stir as this may cause the PDMS to lift off of the substrate. Apply PDMS around the edges of the wafer to ensure that the PDMS membrane remains attached to the substrate.

11. Gently rinse with acetone and isopropyl alcohol and set on flat surface. Air dry.

12. Oxidize PDMS surface again.

13a. Apply $2^{nd}$ layer 17 of PDMS using a stencil-like mask. This mask must be made of a material that sticks to the PDMS enough not to cause seepage of the PDMS under the mask, but can be removed after either spinning or casting the PDMS without ripping or damaging the underlying metalized PDMS membrane. An overhead projector transparency sheet can be used for this purpose.

Figure 7:
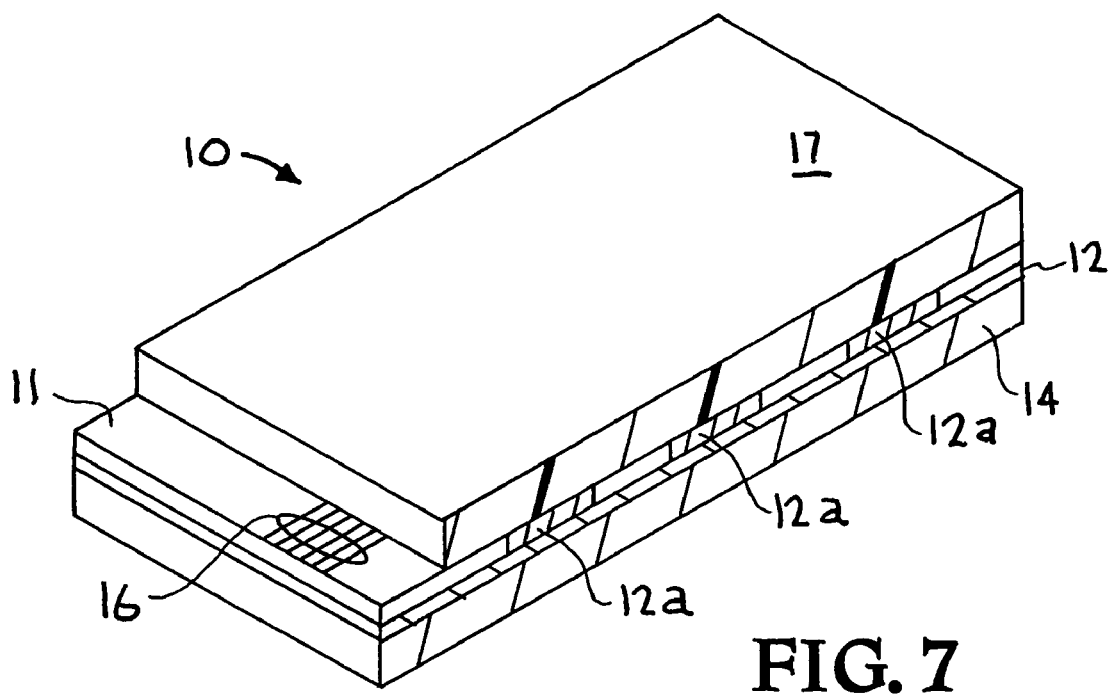
FIG. 7 illustrates a step of an electrode array fabrication process wherein a $2^{nd}$ layer of PDMS is applied.
Figure 8A:
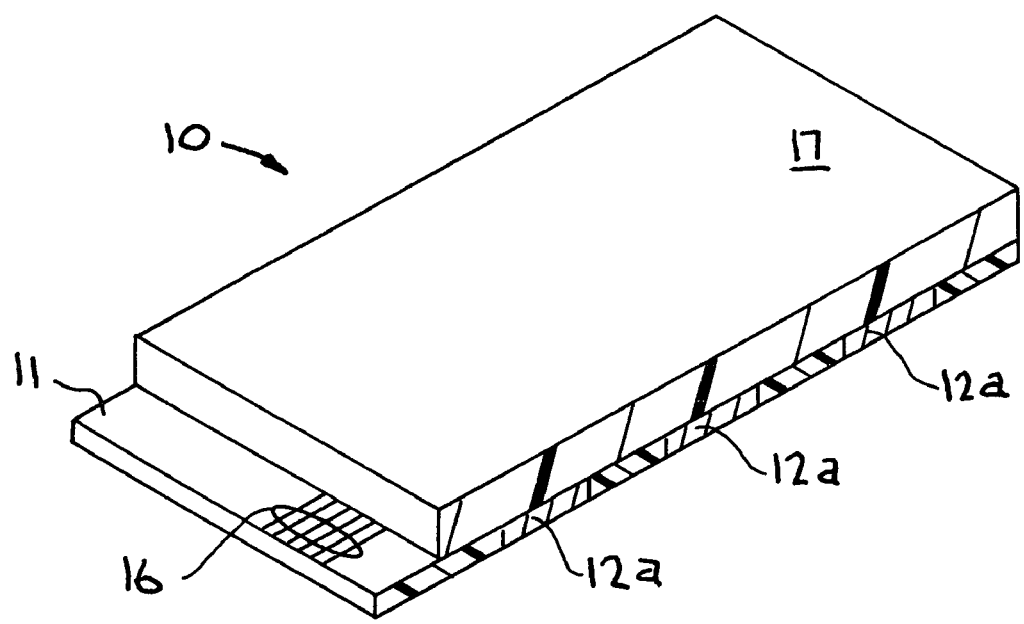
FIG. 8A shows a top view of the device removed from the handle wafer.
Figure 8B:
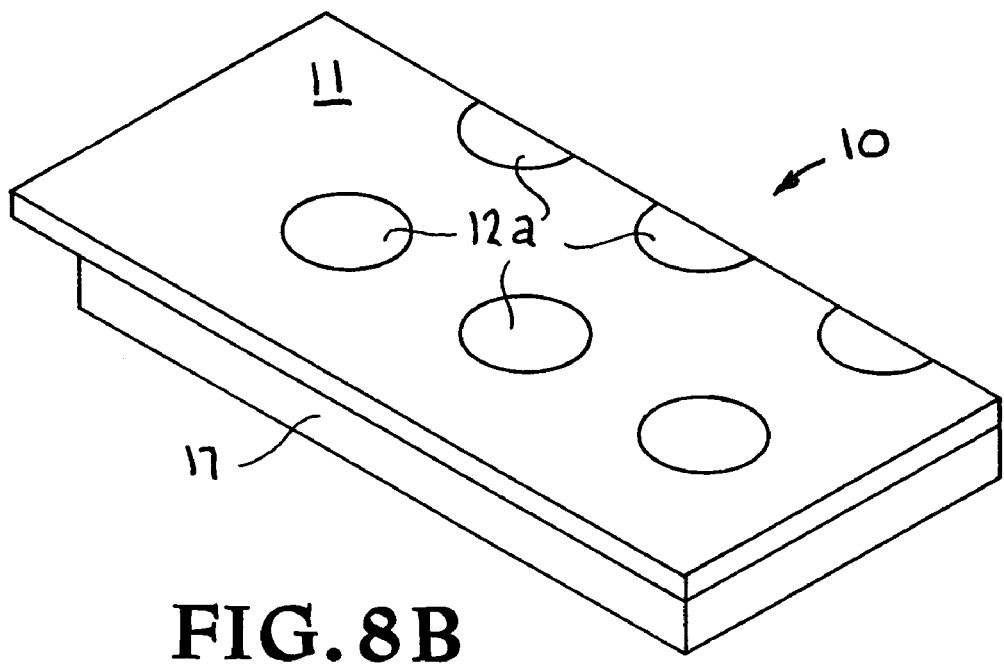
FIG. 8B shows a bottom view of the device removed from the handle wafer.

Cut sections from the mask in regions where the $2^{nd}$ layer of PDMS is desired. Apply the mask to the $1^{st}$ layer of PDMS.
    Spin, cast, or mold PDMS over the mask.
    Remove mask gently.
    Cure at 66° C. for 1 hr.
    Step 13a is illustrated in FIG. 7.
    Remove device 10 from handle wafer as shown in FIGS. 8A and 8B.

13b. A second approach for applying $2^{nd}$ layer of PDMS is by membrane transfer from UV tape, soft substrate, or flexible wafer (examples: Polyimide or transparency)

UV tape example:
    Apply UV tape onto a hard substrate using adhesive side.
    Spin, cast or mold PDMS on non-adhesive side of UV tape.
    Cure at 66° C. for 1 hr.
    Expose the UV tape with UV light.
    Remove tape from hard substrate.
    Oxidize both the PDMS on original wafer and on the UV tape.
    Bond PDMS on tape to PDMS on the handle wafer
    Use razor blade to cut part of the PDMS from the tape
    Peel back the tape slowly
    PDMS that was on the tape is now bonded to PDMS on the handle wafer (See FIG. 7.)
    Remove the device from the handle wafer (See FIG. 8.)

13c. A third approach for applying the 2" layer of PDMS is to partially dip coat the desired area to be encapsulated in PDMS.

Figure 9:
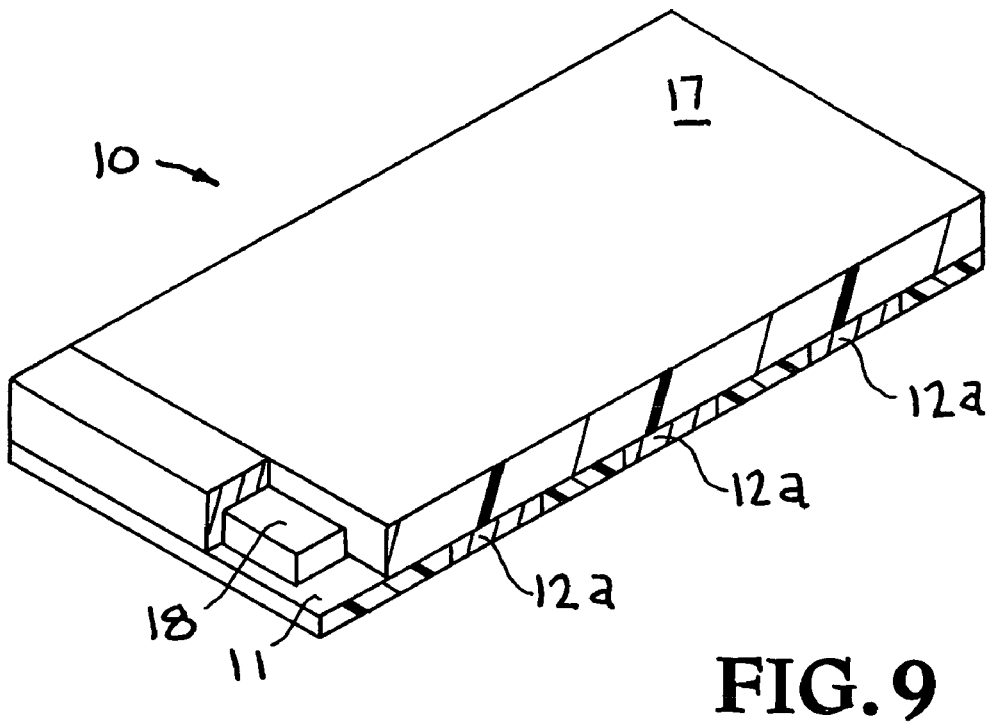
FIG. 9 shows the device with an encapsulated electronic chip 18 attached to the lead lines.

Referring now to FIG. 9, the device 10 is shown with an encapsulated electronic chip 18 attached to the lead lines 16. The device 10 was fabricated as illustrated in FIGS. 1 through 8. The device 10 was fabricated by a method that produces a polymer substrate 11 that has the ability to conform to various shapes of tissue. An electroplating seed layer 12 is deposited onto handle wafer 14. A patterned photoresist is produced. Polymer 15 is spun or cast onto the patterned photoresist on the handle wafer 14. The remaining photoresist is removed resulting in patterned PDMS 11 on top of the handle wafer 14 with sections of the underlying seed layer 12 exposed. Gold or platinum is electroplated through the patterned PDMS to form electrodes 12a. Conductive metal lines 16 are patterned on the PDMS 11. A $2^{nd}$ layer 17 of PDMS is applied. The device 10 is removed from the handle wafer. In one embodiment the device is biocompatable. In another embodiment the device is implantable. In one embodiment the polymer is an elastomer. In another embodiment the polymer is an elastomer that is conformable. In another embodiment the polymer is an elastomer that is flexible and stretchable. In another embodiment the elastomer is poly(dimethylsiloxane). The flexible electrode array 10, shown in FIGS. 1-9 and constructed as described above, was successfully tested.

During implantation or use, it is possible that the electrode array might be stretched. Thus it is important that the device is not only flexible, but is also stretchable. Pull tests were performed to demonstrate that the devices are flexible and stretchable and still maintain conductivity to large strains (up to 3%). Thus, the devices will not fail when handled by the physician for implantation, or when used in applications in which they must deform periodically, for example if attached to the skin. Even when the devices are stretched to the point where the conducting lines fail, with time they regain their conductivity. This is due to the viscoelastic nature of the PDMS. When metalizing the PDMS, there are several factors that contribute to the ability to create robust conducting lines. When the PDMS is spin-coated onto a substrate, it has a built-in tensile residual stress (the PDMS wants to contract, but is constrained by the substrate). This occurs because of the volume change associated with curing the PDMS. When removed from the handle wafer, the PDMS contracts and the tensile stress relaxes. Depositing a metal film with compressive residual stress (the film wants to expand) onto the PDMS before release from the handle wafer results in wrinkling of the metal. The metal becomes even more wrinkled when the PDMS contracts after release from the handle wafer. The combination of these two effects results in metal conductors that can be stretched without breaking after releasing the load. Even if stretched to the point where the metal breaks, when the load is released, the PDMS substrate contracts and the broken conducting lines reestablish contact.

Figure 10:
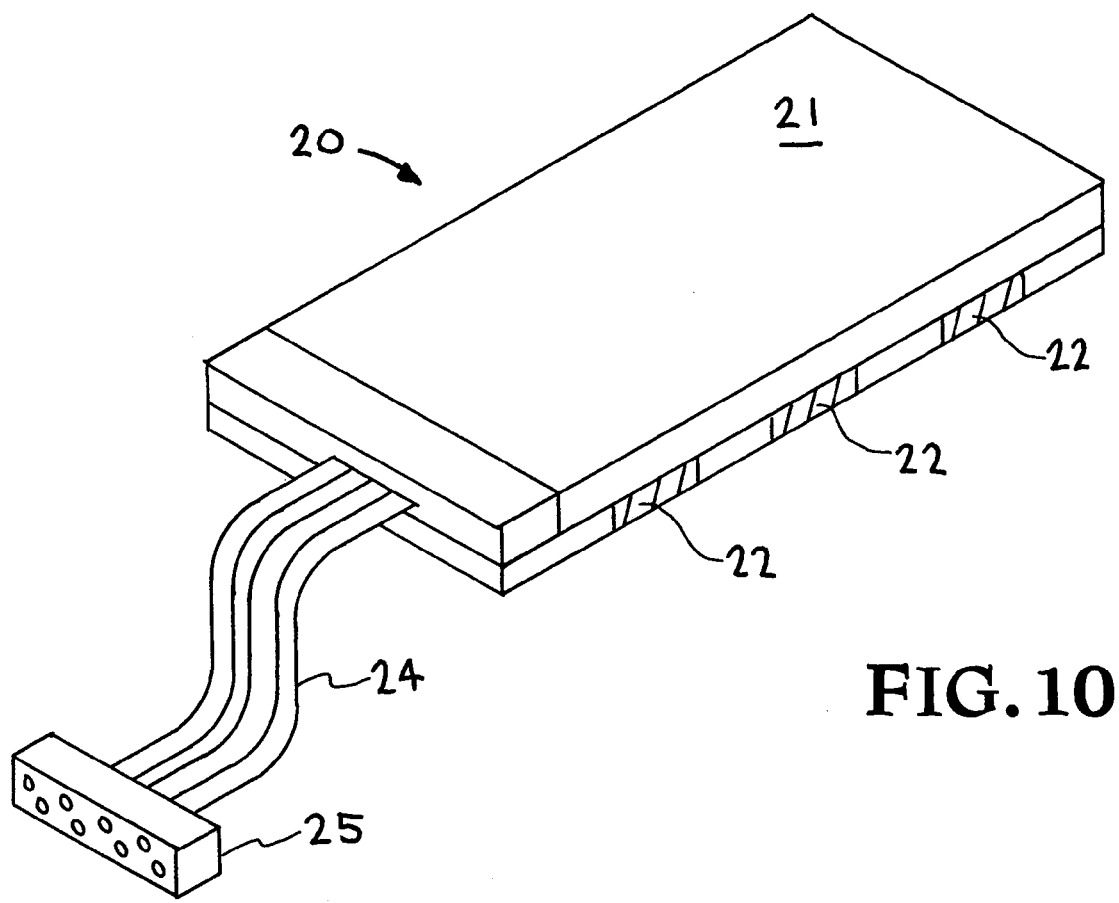
FIG. 10 illustrates another embodiment of an electrode array of the present invention.

FIG. 10 illustrates another embodiment of an electrode array of the present invention. This embodiment of the flexible electrode array system is generally designated by the reference numeral 20. The flexible electrode array 20 is produced by the steps illustrated in FIGS. 1-8 and described above. The electrode array 20 utilizes a substrate 21 made of a compliant material. Electrodes 22 are embedded in the substrate 21. Conductive leads 23 are connected to the electrodes 22 and to a ribbon cable 24. The ribbon cable 24 includes a connector 25 for connecting the electrode array 20 to other electronics. For example, the connector 25 may be connected to a device for transferring an image signal to tissue in a retina. The ribbon cable 24 also could be fabricated using the same process described above for PDMS with embedded conducting lines. In this embodiment, the implanted electrode array and ribbon cable form one continuous device.

Figure 11A:
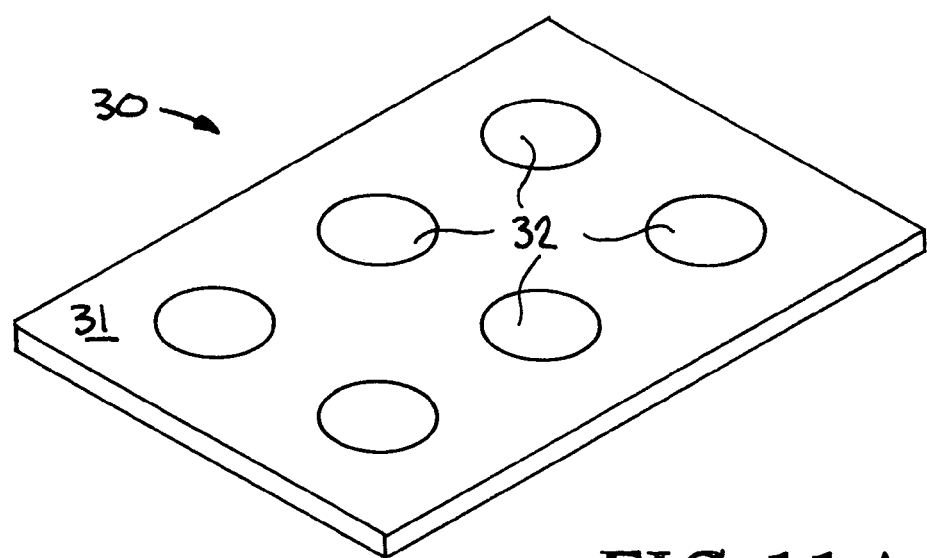
FIGS. 11A and 11B show another embodiment of an electrode array of the present invention.
Figure 11B:
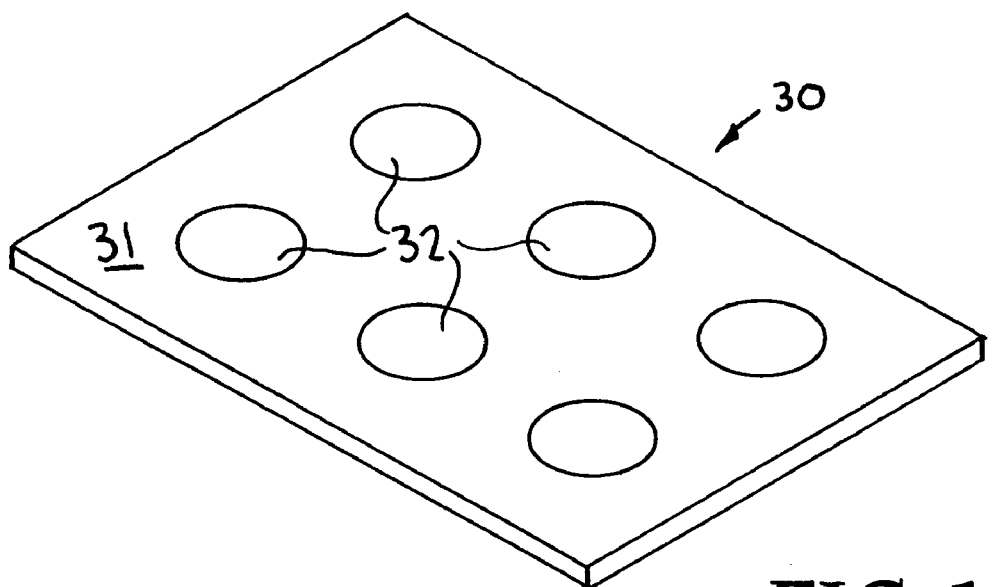

Referring now to FIGS. 11A and 11B, an embodiment of a metalized PDMS device is shown. This embodiment is designated generally by the reference numeral 30. An upper view of the electrode array 30 is show in FIG. 11A and a lower view is shown in FIG. 11B. Electrodes 32 extend through the substrate 31.

The substrate 31 is compliant. In one embodiment the substrate is composed of an elastomer and has the ability to conform to the shape of tissue. The elastomer can be poly (dimethylsiloxane) or PDMS.

Description of an Embodiment for Artificial Vision

One embodiment of the present invention provides an intraocular prosthesis. This provides a system that restores vision to people with certain types of eye disorders. An image is captured or otherwise converted into a signal representing the image. The signal is transmitted to the retina utilizing an implant. The implant consists of a polymer substrate. In one embodiment the polymer substrate is flexible and stretchable and has the ability to conform to the shape of the retina. Electrodes are embedded in the polymer substrate. Conductive leads are connected to the electrodes for transmitting the signal representing the image to the electrodes. The electrodes embedded in the polymer substrate contact the retina and the signal representing the image stimulates cells in the retina. In one embodiment the device for capturing a signal representing the image is a video camera and the signal is relayed to the electrode array via wires, or by a wireless link. In one embodiment the electrodes include micromachined points, barbs, hooks, and/or tacks to attach the array to the retinal tissue. In one embodiment the polymer is liquid silicone rubber (LSR). In one embodiment the polymer is poly (dimethylsiloxane).

Figure 13:
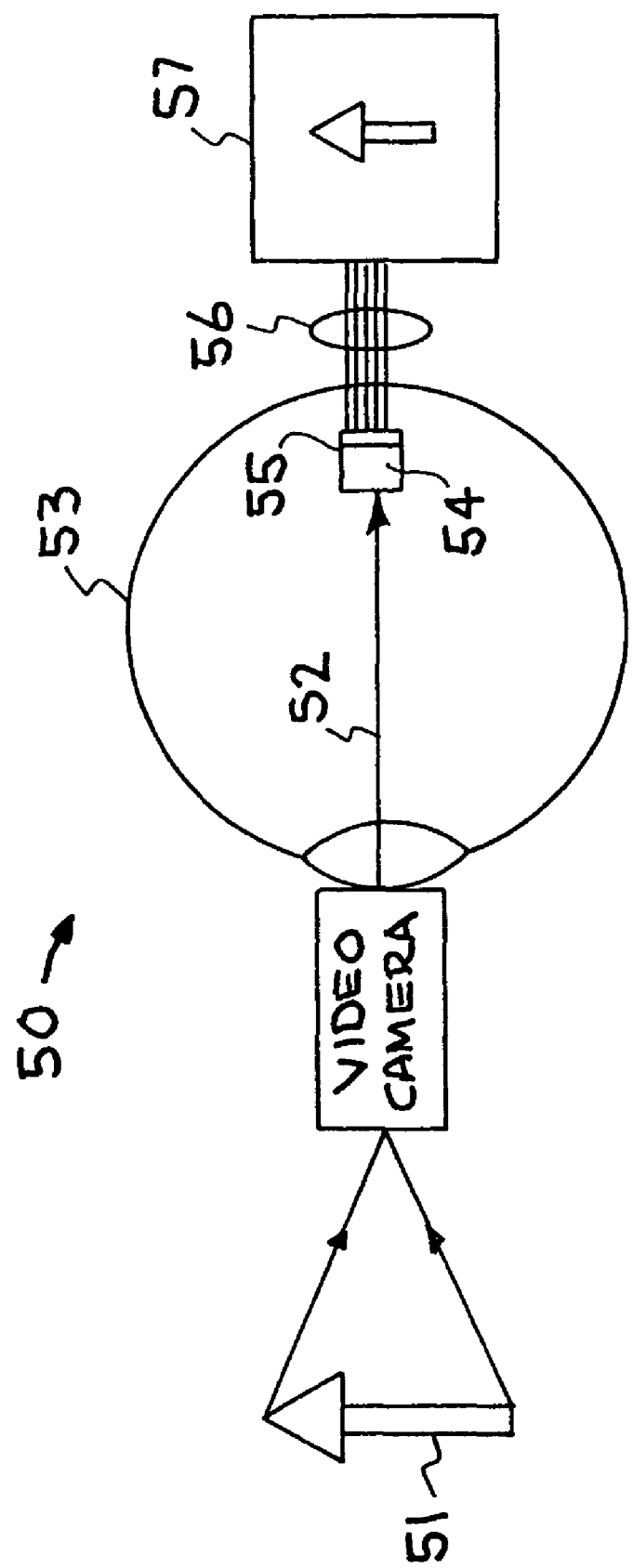
FIG. 13 illustrates an artificial vision system.

FIG. 13 illustrates an intraocular prosthesis. This is an embodiment of the present invention that provides a system that restores vision to people with certain types of eye disorders. The system is generally designated by the reference numeral 50. A video camera captures an image 51. A device sends the image via cable connection, a laser or RF signal 52 into a patient's eye 53. Electronics 54 within the eye 53 receive the image signal 51 and send it to the electrode array 55. The implant 54 includes an electrode array 55 utilizing a substrate made of a compliant material with electrodes and conductive leads embedded in the substrate. The electrodes contact tissue of the retina. The implant 54 stimulates retinal neurons. The retinal neurons transmit a signal to be decoded to the brain 57.

The present invention provides an artificial vision system that can help restore vision to people left totally or partially blind by retinal degeneration or other retinal diseases. In retinitis pigmentosa (RP), the progression of the disease can be slow, but eventually can lead to total blindness. However, some of the inner nuclear layer cells and some of the ganglion cells remain viable, and it may be possible to restore vision through stimulation of these cells.

Even when photoreceptor cells have been lost, the retinal cells are often still viable. Directly stimulating these cells may restore vision to patients suffering from photoreceptor degeneration. Localized electrical stimulation to the retina induces light perception in patients blind from outer retinal degenerations. Small patterns can be recognized through stimulation with multielectrode arrays. Thus, an implanted visual prosthesis appears promising.

Referring again to FIG. 13, the video camera captures the image 51. The image is sent via wire, a laser or RF signal 52 into the eye 53 to the implant 54. The implant 54 is connected to the retina by electrodes. The implant 54 stimulates retinal neurons. The retinal neurons transmit the signal to be decoded. The system senses an image and stimulates the retina with a pattern of electrical pulses based on the sensed image signal. The implanted component 54 receives the transmitted signal, derives power from the transmitted signal, decodes image data, and produces an electrical stimulus pattern at the retina based on the image data.

The implant 54 includes an electrode array of poly(dimethylsiloxane) (PDMS, a form of silicone rubber) for the substrate. The substrate includes embedded electrodes and conductive leads for directly stimulating cells in the retina and transmitting a visual image. The fact that the device is flexible and can conform to the shape of the patient's retina is highly advantageous. The device is stretchable, making it rugged during handling, insertion, and use. PDMS is oxygen-permeable but absorbs very little water, two properties that are advantageous for a biological implant. PDMS is an example of a material that works well for this application, but other polymers also could be used.

The flexible, stretchable electrode arrays have many uses, including shaped acoustic transducers, and formed biological sensors and stimulators for interfacing with the human body.

These can be used for applications ranging from non-destructive evaluation to sensors and stimulators for virtual reality simulators.

The present invention provides a method for fabricating flexible electrode arrays using PDMS (silicone) substrates. The devices have embedded electrodes and conducting lines for transmitting signals to cells in the eye. The fact that the devices are flexible allows them to conform to the shape of the retina without damaging cells.

Figure 12:
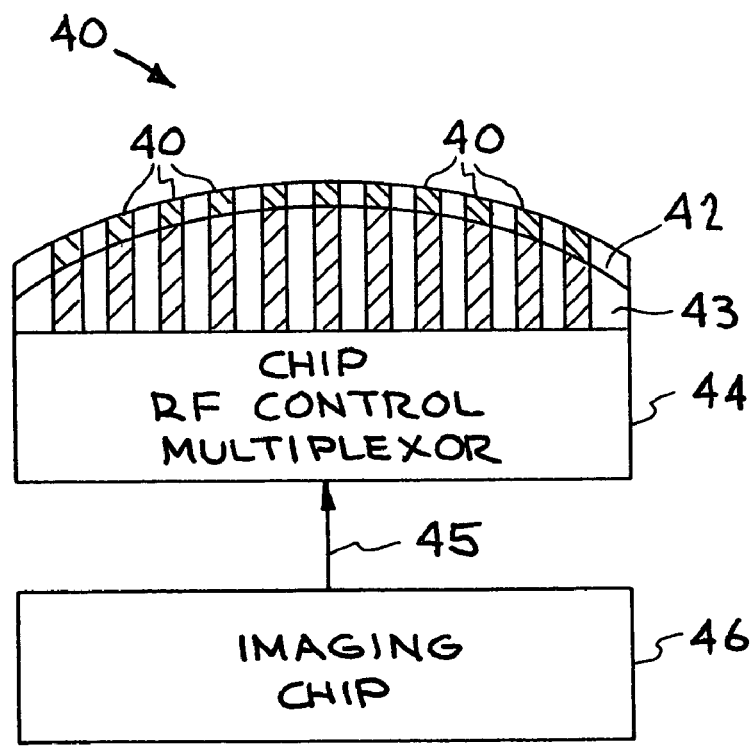
FIG. 12 illustrates an intraocular prosthesis.

Referring now to FIG. 12, a concept diagram illustrates the technical approach of an electrode array 40 of the present invention. As shown in FIG. 12, an imaging chip 46 transmits a signal representing an image to RF control unit 44 through an RF link 45. The RF control unit 44 is connected to an interface contact 43. The interface contact unit 43 is connected to a conformable PDMS substrate 42. The conformable PDMS substrate 42 has embedded microstimulator electrodes 41. The microstimulators 41 connect the implant to the retina. The electrodes 41 stimulate the retina with a pattern of electrical pulses based on the sensed image signal. The implant receives the transmitted signal, derives power from the transmitted signal, decodes image data, and produces an electrical stimulus pattern at the retina based on the image data.

In order to realize an array of microelectrodes, several microelectronics and micromechanical systems (MEMS) processing approaches are applied. These technologies help enable artificial sight. The following engineering characteristics are included in the implantable electrode array:

1. Platinum electrodes with photolithographically defined features including micron-scale contacts for precision stimulation, tailored impedance for overall systems matching requirements, and micromachined barbs, hooks or tacks for anchoring the implant to the retina.

2. A flexible biocompatible electrode substrate measuring approximately 4 mm×4 mm×0.1 mm that can be easily inserted and positioned according to the contour of the inner eye.

3. An electrical interconnection array for interfacing with a regulated current drive derived from the processed image of the receiver chip as shown in FIG. 12. This device consists of a micromachined conformable electrode surface hybrid-bump bonded to a second RF control circuit that applies electrical signals derived from the sensed image. FIG. 12 shows electrical connections through the back of the implant. Other ways can be used to interface to the electronics chip. For example, leads from the back of the electrode array can connect to an array of bond pads on the same PDMS substrate, and the electronics chip can be flip-chip bonded to the bond pad array. The electronics chip can be embedded in the PDMS, forming a single, integrated, implantable device.

4. All electrical leads and circuits except the electrode contacts will be embedded in the PDMS substrate. Thus, the PDMS forms a biocompatible package.

Photolithographically-Defined Microelectrodes

Several groups have used MEMS fabrication approaches to realize microelectrodes for a variety of applications including neurostimulation. These approaches have been primarily based on the use of photolithographically-defined silicon. While offering the capability of precise local electrical stimulation, the inherent brittleness of silicon as an electrode is a significant reliability concern that necessitates the consideration of other materials approaches, particularly in applications such as retinal implants where microelectrode breakage could have significant medical consequences.

Materials such as platinum, titanium, and iridium oxide can be prepared by sputtering, electron beam evaporation, and electroplating. An important approach described for fabricating the above neurostimulator array lies in the use of PDMS as the starting material substrate. The conformable nature of the PDMS material is important in order to ensure stable and uniform mechanical contact with retinal tissue. Technical approaches based on the use of traditional silicon substrates are limited due to the mechanical rigidity and fragility of silicon.

Previous experience in processing this material for other BioMEMS applications has shown this material to be remarkably easy to deposit, pattern, and handle. PDMS allows the mechanical flexibility, robustness, and strechability required for placement in full area contact according to the shape of the retina. Attachment holes for sutures or tacks can easily be formed in the PDMS substrate by simple spacer castings. In addition, barbs or hooks or tacks can be formed on the surface of the PDMS using a suitable mold, or can be made of other materials and embedded within the PDMS.

Electrical Interfacing Between the Electrode Array and Image Processing Chip

Electrical interconnection between the stimulation electrode array and front-end electronics presents unique challenges in this implantable biomedical device application. For the retinal prosthesis application an encoded RF broadcast signal is used to communicate an image pattern to a multiplexor. The multiplexor in turn sets a pattern on temporal current pulses that drives the electrode array. The main advantage of this approach lies in the use of a short-range RF broadcast signal (~1 cm). This eliminates the need for mechanical wire interconnections that are subject to failure and present significant packaging problems. A second RF signal applied external to the eye is used to charge storage capacitors that ultimately deliver current to the electrode array.

Electrode interconnections must be mechanically robust to prevent breakage, exhibit characteristics of an ideal electrical conductor, and provide isolation from the biological environment within the eye. Bump bonding the integrated circuit chip onto the microelectrode array device, then encapsulating in PDMS addresses both of these issues. The IC chip can be directly bonded to the back of the electrode array, with an optional interface chip, or can be bonded to the side of the electrode array with conducting leads delivering the signal to the electrodes.

Figure 14A:
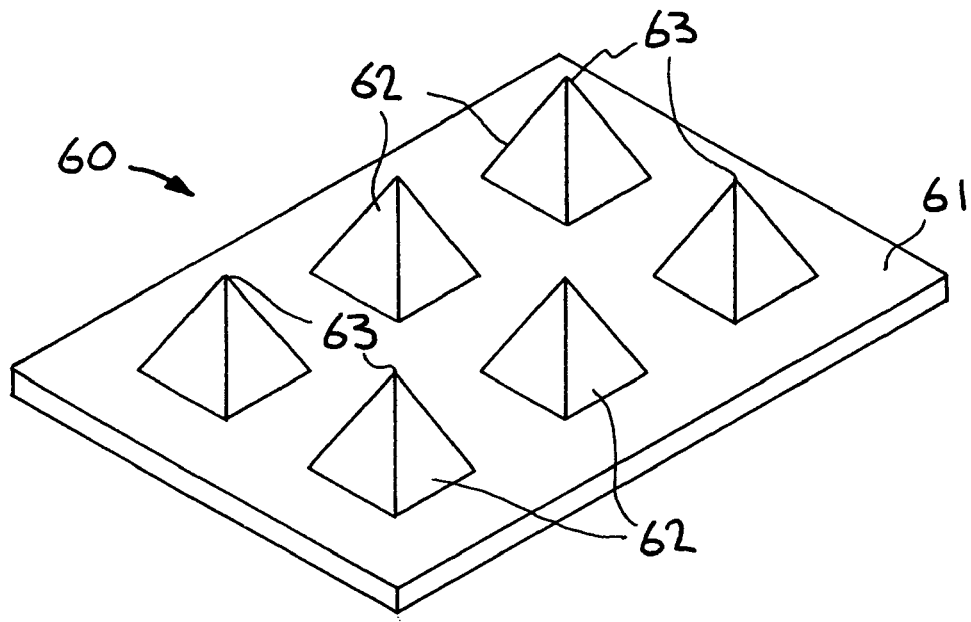
FIGS. 14A and 14B illustrate embodiments of the electrode array that include microfabricated features for improving the way the electrode array contacts tissue.
Figure 14B:
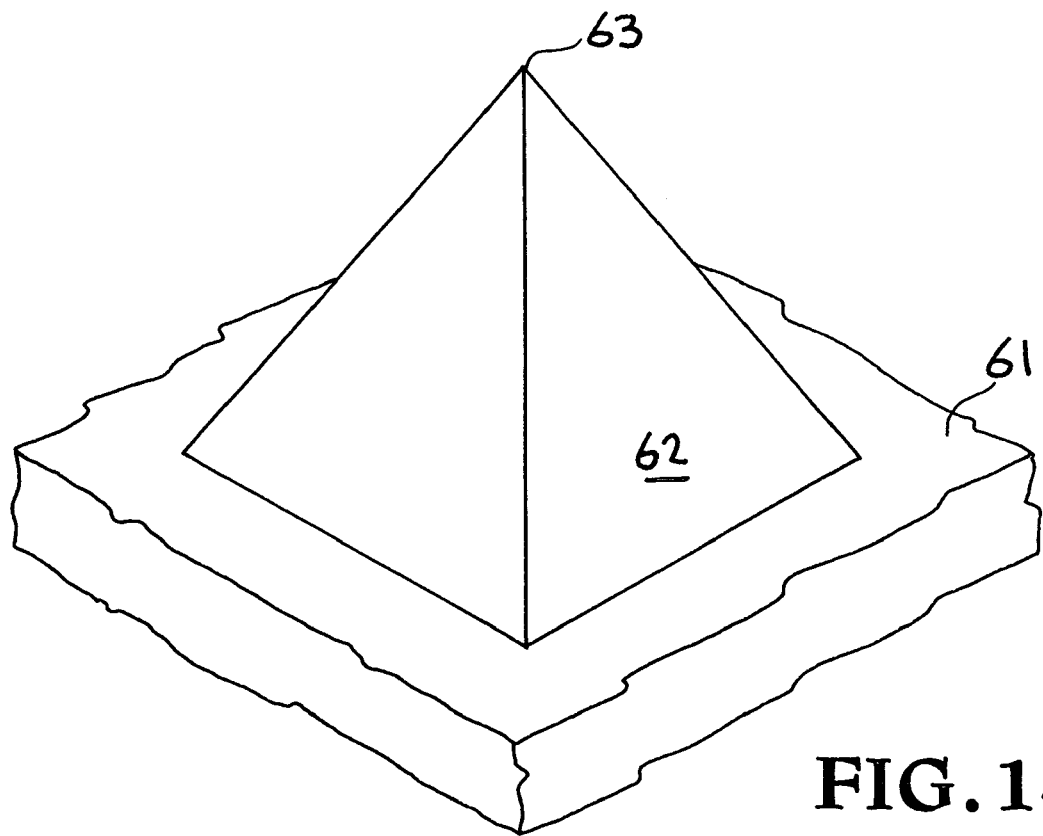

Referring now to FIGS. 14A and 14B, embodiments of the electrode array are illustrated that include structures for improving the way the electrode array contacts tissue. One use of the electrodes is targeting specific areas in the retina without tearing or damaging the tissue or cells. The system, generally designated by the reference numeral 60, uses a PDMS substrate 61 with embedded electrodes 62. The electrodes are micromachined to produce points, barbs, hooks, or tacks. As shown in FIGS. 14A and 14B the surface of the electrode contains sharp points. The microfabricated electrode arrays illustrated in FIGS. 14A and 14B demonstrate that it is possible to obtain sharp, compliant features 63 in the PDMS 61. It is also possible to produce barbs, hooks, or tacks on or adjacent to the electrodes using micromachining technology.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system of fabricating a flexible electrode array, comprising the steps of:
    spin-coating a poly(dimethylsiloxane) layer (PDMS) onto a handle wafer that has been pre-coated with a conductive seed layer;
    patterning said poly(dimethylsiloxane) layer to expose said conductive seed layer to form electrodes;
    plating a material for said electrodes until said electrodes are higher than a thickness of said poly(dimethylsiloxane) layer and until said electrodes form mushroom caps which later will prevent said electrodes from popping out of said poly(dimethylsiloxane) layer when said poly(dimethylsiloxane) layer is removed from said handle wafer; and
    patterning conducing lines on said poly(dimethylsiloxane) layer.

2. The system of fabricating a flexible electrode array of claim 1, wherein said step of patterning conducing lines on said PDMS is conducted using thin film deposition.

3. The system of fabricating a flexible electrode array of claim 1, wherein said step of patterning conducing lines on said PDMS is conducted using photolithography.

4. The system of fabricating a flexible electrode array of claim 1, wherein said step of patterning conducing lines on said poly(dimethylsiloxane) layer is conducted using shadow masking.

5. The system of fabricating a flexible electrode array of claim 1, further comprising a step of directly embedding an electrical connector into said poly(dimethylsiloxane) layer to interface with electronics.

6. The system of fabricating a flexible electrode array of claim 1, further comprising a step of casting a PDMS capping layer to said PDMS.

7. The system of fabricating a flexible electrode array of claim 1, further comprising a step of bonding a poly(dimethylsiloxane) capping layer to said poly(dimethylsiloxane) layer.

8. The system of fabricating a flexible electrode array of claim 1, wherein said conductive seed layer is made of biocompatible.

9. The system of fabricating a flexible electrode array of claim 1, wherein said conductive seed layer is made of gold.

10. The system of fabricating a flexible electrode array of claim 1, wherein said conductive seed layer is made of platinum.

11. The system of fabricating a flexible electrode array of claim 1, wherein said conductive seed layer is made of a conductive polymer material.

12. The system of fabricating a flexible electrode array of claim 1, wherein in said step of plating a material for said electrodes until said electrodes are higher than the thickness of said poly(dimethylsiloxane) layer and until said electrodes form mushroom caps which later will prevent said electrodes from popping out of said poly(dimethylsiloxane) layer when said poly(dimethylsiloxane) layer is removed from said handle wafer and said electrodes are gold electrodes electroplated onto said conductive seed layer.

13. The system of fabricating a flexible electrode array of claim 1, wherein the material is made of platinum electroplated onto said conductive seed layer.

14. The system of fabricating a flexible electrode array of claim 1, further comprising a step of directly embedding an integrated circuit into said poly(dimethylsiloxane) layer such that said integrated circuit interfaces with the electrode array.

* * * * *